United States Patent [19]

Chirife

[11] Patent Number: 5,154,171
[45] Date of Patent: Oct. 13, 1992

[54] RATE ADAPTIVE PACEMAKER CONTROLLED BY EJECTION FRACTION

[76] Inventor: Raul Chirife, Pirovano 137, 1640 Martinez, Buenos Aires, Argentina

[21] Appl. No.: 714,580

[22] Filed: Jun. 15, 1991

[51] Int. Cl.$^5$ .......................................... A61N 1/362
[52] U.S. Cl. ............................................. 128/419 PG
[58] Field of Search ............................. 128/419 PG

[56] References Cited

U.S. PATENT DOCUMENTS

| | | | |
|---|---|---|---|
| 4,535,774 | 8/1985 | Olson | 128/419 PG |
| 4,730,619 | 3/1988 | Koning et al. | 128/419 PG |
| 4,773,401 | 9/1988 | Citak et al. | 128/419 PG |
| 4,802,481 | 2/1989 | Schroeppel | 128/419 PG |

Primary Examiner—William E. Kamm
Assistant Examiner—Scott M. Getzow
Attorney, Agent, or Firm—Haugen and Nikolai

[57] ABSTRACT

A rate adaptive pacer designed to accommodate changes in a patient's metabolic demand utilizes ventricular ejection fraction (EF) as the rate controlling parameter. Ejection fraction is measured by sensing intracardiac impedance at end-diastole and end-systole and then using these measurements to compute stroke volume (SV). Ejection fraction is the stroke volume divided by the end-diastolic volume. This calculated value of EF is processed by the pacemaker to determine the escape interval (pacing rate) through a simple conversion algorithm.

10 Claims, 3 Drawing Sheets

RATE ADAPTIVE PACEMAKER CONTROLLED BY EJECTION FRACTION

BACKGROUND OF THE INVENTION

I. Field of the Invention

This invention relates generally to the design of cardiac pacemakers and more particularly to the timing control of a rate adaptive cardiac pacer in which the control signal for the timing circuit is derived from the ventricular ejection fraction (EF) of a beating heart and, accordingly, is responsive to metabolic demand.

II. Discussion of the Prior Art

It is well known that patients suffering from severe bradycardia or chronotropic incompetence can be helped by an implanted cardiac pacemaker designed to restore a normal, at-rest, heart rate. Typical prior art pacemakers will usually have a fixed rate or a narrow range of externally programmable rates so that they also prove efficacious in meeting metabolic demand at low levels of exercise. However, the inadequacy of such fixed rate pacers to meet metabolic demands at-rest and during exercise led to the development of a class of pacemakers referred to as "rate adaptive pacemakers". In this latter class of pacemakers, a means is provided for sensing a parameter that changes with metabolic demand and then the sensed value is used to alter the rate at which cardiac stimulating pulses are produced.

Prior art pacers assess metabolic demand through a variety of techniques or approaches. For example, such parameters as blood pH, blood temperature, QT interval, physical activity, respiration rate as well others have been disclosed in the prior art. Such pacemakers are considered as an improvement over the earlier fixed rate devices, but the majority of rate adaptive pacers now available suffer either from a lack of sensitivity to changing conditions, a lack of specificity or a lack of sufficient speed in response to changes in metabolic need. An example of a pacemaker that suffers from a lack of specificity is the Activitrax TM pacemaker sold by Medtronic Inc. That device uses a motion transducer to develop the control signal for modifying the pacemaker's stimulating rate. Difficulty arises in distinguishing body motion or vibration from artifacts produced by passive vibration or by motion that is not associated with an increase in metabolic demand. For example, a patient with such an activity-based sensor may be riding in a vehicle and sitting quietly, but if that vehicle should be traveling on a bumpy road, the pacing rate will inappropriately accelerate. Other relatively non-specific pacemakers are those that base the rate change on respiration parameters, such as chest impedance. The respiratory impedance signal obtained in this manner may be contaminated by motion artifacts. One example of such an artifact is the additive effect of arm movements, which unduly accelerate the rate beyond that which is dictated by the prevailing metabolic needs of the patient. In this system, to detect chest impedance, impedance plethysmography is used in which a constant current carrier signal is permanently required which detracts from the life of an implanted battery-type power source.

Temperature-controlled rate adaptive pacemakers are examples of those lacking sensitivity. This is due to the normal physiologic lag between onset and level of exercise and the point at which the body temperature rises an amount that will trigger the increase in the pacemaker's stimulating pulse rate. This slow response can also be unpredictable.

Pacemakers using the QT interval as a control parameter are also found to be quite slow in reacting to changes in metabolic demand and tend to be non-specific and somewhat erratic. Self-acceleration is common in such pacemakers, because the physiologic signal used for rate control predisposes them to positive feedback and, thus, instability.

The most accurate and physiologic systems are those that use intracardiac signals, especially those that are ventricular volume-derived, e.g., stroke volume, dV/dt, pre-ejection period. The stroke-volume controlled rate responsive pacemaker, as shown in the Olson U.S. Pat. No. 4,535,774, in the Salo U.S. Pat. No. 4,686,987 and in the Schroeppel U.S. Pat. No. 4,802,481, each suffer from a lack of specificity, since they tend to be preload-dependent. Cardiac preload can be defined as the volume of blood that returns to the heart from the circulation. Venous return is strongly influenced by cardiac cycle length (the longer the diastole, the larger the volume-per-beat), respiration, and especially postural changes, none of which truly reflect a change in metabolic demand.

Stroke volume controlled rate adaptive pacemakers are based on the relationship that normally exists between stroke volume, heart rate, cardiac output and metabolic demand. Thus, in the case of a normal healthy individual undergoing exercise, stroke volume, i.e., the amount of blood ejected in each heart beat, remains relatively constant or increases very little. The increase in cardiac output in this case is caused almost exclusively by the heart rate increase (cardiac output = stroke volume × heart rate). In patients with complete heart block, who are unable to undergo an increase in heart rate in proportion to increased metabolic demands, have increased cardiac output due to increased stroke volume. That is, the blood ejected with each heart beat is augmented in proportion to metabolic need. Conversely, if heart rate is artificially increased with the patient at-rest (for example, by pacing without a corresponding increase in metabolic need), there will be a decrease in stroke volume, keeping the product of the two, i.e., cardiac output, constant.

The algorithm of stroke volume-based rate adaptive pacemakers calls for an increase in pacing rate whenever there is an increase in stroke volume, and a slowing of pacing rate when stroke volume decreases. The endpoint, then, is to keep stroke volume constant. Such an algorithm would be appropriate, were there are no concurrent factors, such as, postural changes, respiration, cough, etc., which strongly affect venous return to the right heart (and hence change stroke volume) without any concomitant change in metabolic need. For example, if a patient with a stroke volume-based rate adaptive pacemaker goes from the standing to the recumbent position, there will be a sudden increase in venous return to the heart, with blood from the lower extremities augmenting stroke volume. This leads to an increase in the pacing rate which is unnecessary and non-physiologic. Normal individuals react in just the opposite way. If the same subject stands up, there will be blood pooling in the lower extremities, causing a reduction in venous return to the heart. This will produce a reduction in stroke volume, which, according to the pacemaker algorithm, will effect a reduction in pacing rate, which is just the opposite of what should have happened.

It can be seen, then, that stroke volume is dependent on end-diastolic volume (EDV), a reflection of preload or venous return, and the contractile force of the heart (contractility). In the absence of metabolic-mediated contractility changes, variations of stroke volume are largely related to the so-called Frank-Starling law of the heart which states that the greater the cardiac muscle fiber stretch (produced by preload), the greater the stroke volume. Stated otherwise, the volume of blood ejected per beat will be proportional to the volume of blood contained in the ventricle at end-diastole.

One way of diminishing the influence of preload on stroke volume is by simultaneously taking into account the end-diastolic volume of the same beat. By determining the ratio of stroke volume to end-diastolic volume, it is possible to assess more accurately the contractility effect on changing volumes. This ratio is called the ejection fraction (EF), and is normally expressed as a percentage of the end-diastolic volume ejected from the ventricle. Ejection fraction is, thus, less dependent on preload and is a more accurate estimate of cardiac contractility than stroke volume alone. The same is true for a counterpart of ejection fraction, the residual fraction, also indicative of the contractile state of the heart. The residual fraction is the percentage of blood remaining in the ventricle after ejection has finished.

As is described in the prior art patent to Olive, et al., U.S. Pat. No. 4,733,667, indirect measures of the heart's contractility state may be useful signals in controlling the rate at which a rate adaptive pacemaker will operate. Pre-ejection period and rate of change of pressure or volume with respect to time are examples of indirect contractility indicators.

OBJECTS

It is accordingly a principal object of the present invention to provide an improved rate adaptive pacemaker.

Another object of the invention is to provide a rate adaptive pacemaker which is more sensitive to changing conditions and more specific to changes in metabolic need than prior art pacemakers.

A further object of the invention is to provide a rate adaptive pacer in which ejection fraction is employed as the rate determining parameter.

SUMMARY OF THE INVENTION

The foregoing objects, features and advantages of the invention are achieved by providing a novel rate adaptive pacemaker using ventricular ejection fraction, which is a volume-derived indicator of the demands imposed upon the heart by metabolic need of the body. Using EF as the control signal injected into the timing circuit of a standard rate adaptive pacemaker enhances its ability to respond in direct relation to the patient's changing metabolic needs as he or she performs daily activities. In accordance with the invention, an intracardiac impedance sensing lead is disposed in either the right or left heart and a carrier oscillator is arranged to apply a relatively high frequency constant current signal between a pair of drive electrodes on the lead. A sense amplifier is connected across a second pair of electrodes which may also be disposed on the lead. The output from the sense amplifier comprises a modulated carrier signal where the modulation is attributable to the systolic action of the heart.

The amplitude of the modulated carrier signal is sampled at the time of occurrence of a natural R-wave or of a paced beat and the amplitude at that time is representative of the diastolic level. The detection of a R-wave or a paced beat also initiates the running of a timer and when a predetermined time period has elapsed, e.g. 200 ms, the modulated carrier signal is again sampled, the sample this time being representative of systolic level. means are also provided to detect the largest deflection of the carrier during systole, corresponding to the value of end-systolic volume. Means are provided for computing the ejection fraction as the difference between the systolic level and the diastolic level divided by the diastolic level. The resulting quantity is then utilized by an algorithm for adjusting the escape interval of the pacing pulse generator.

The system of the present invention may be implemented using analog circuitry or may comprise a digital, microprocessor-based device.

The value of ejection fraction is well known for assessment of cardiac contractile state in clinical cardiology. By dividing end-diastolic volume into stroke volume, the influence of preload on stroke volume is greatly reduced, allowing a better estimation of the contractile state. Since the relationship between end-diastolic volume and stroke volume is non-linear, a more elaborate correction factor may be in order. In the present invention means are provided to correct for non-linearities in the SV/EDV relationship.

Although both right and left heart ejection fraction may be used for rate control, for the sake of simplicity only the right heart parameters will be described herein. In addition, the residual fraction (or end-systolic volume) has similar implications as ejection fraction, and can be measured and a rate adaptive pacer using residual fraction or end-systolic volume as the rate controlling parameter can be implemented in very similar ways. The device of the present invention is capable of operating in most of the available modes (VVIR, DDDR, DDIR, AAIR), and has provision for multi-programmability, data storage, bidirection telemetry, among other standard functions.

DESCRIPTION OF THE DRAWINGS

The foregoing objects, advantages and features of the invention will be better understood from the following detailed description of the preferred embodiment, especially when considered in conjunction with the accompanying drawings in which.

DESCRIPTION OF THE PREFERRED EMBODIMENT

In order to measure ejection fraction (EF) or residual fraction, the preferred embodiment may use any method suitable for measuring or estimating cardiac volumes. However, for clarity, the preferred embodiment will be described as employing the intracardiac impedance technique for estimation of relative end-diastolic volume, end-systolic volume, the difference between the two, i.e., stroke volume (SV), the ratio SV/EDV which is the ejection fraction and the ratio ESV/EDV which is the residual fraction.

Figure 2:
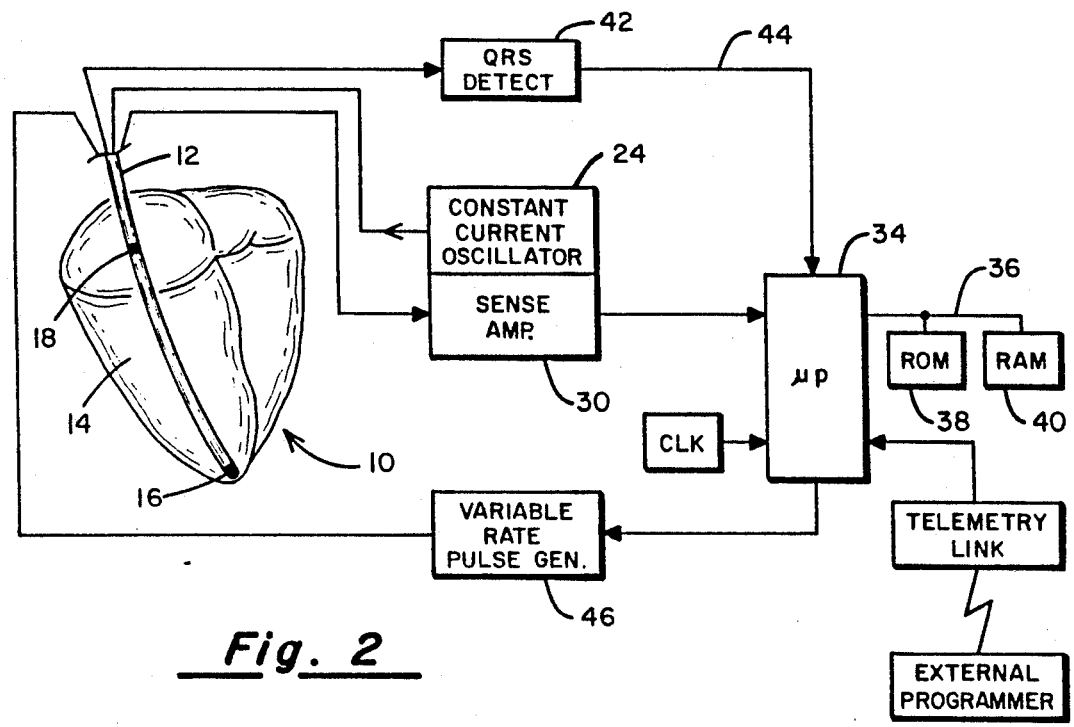
FIG. 2 is a schematic block diagram of a first embodiment of the invention.

With this in mind and with reference to FIG. 2, there is indicated generally by numeral 10 a heart having a catheter or pacing lead 12 inserted into the right ventricle 14. The lead 12 carries 2 of electrodes including a tip electrode 16 disposed near the apex of the heart, and a proximal electrode 18 disposed in the right ventricular cavity. By connecting a high frequency oscillator having a constant current characteristic between proximal electrode 18 and the tip electrode 16, a signal can be derived proportional to the instantaneous impedance developed between these electrodes. In FIG. 2, the constant current oscillator is identified by numeral 24.

Figure 1:
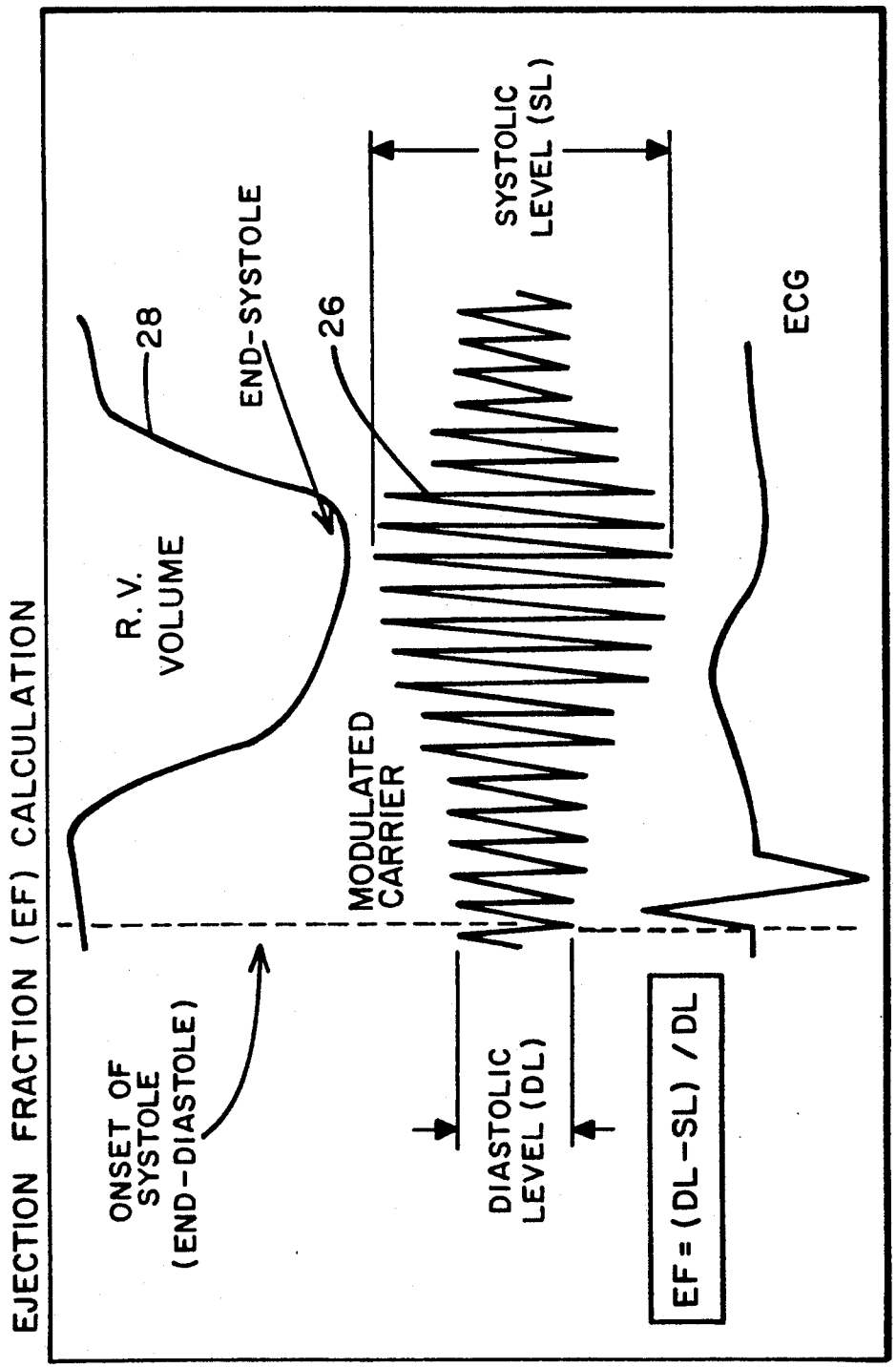
FIG. 1 illustrates a series of waveforms helpful in understanding the principles of operation of the preferred embodiment of the present invention.

With reference to FIG. 1, the carrier signal from the oscillator 24 is amplitude modulated by systolic events. That is to say, the in-flux and outflow of blood from the right ventricle causes the carrier signal to be amplitude modulated as indicated by the waveform 26. Waveform 28 depicts the variation of right ventricular volume during one cardiac cycle. It can be seen that at end-diastole when the ventricular chamber is filled with blood, the sensed impedance is low. As blood flows out of the heart, the impedance increases and is a maximum at end-systole where the blood volume remaining in the ventricle is a minimum. The difference between the maximum peak impedance and the minimum peak impedance is proportional to the stroke volume of the heart. By dividing stroke volume by the end-diastolic volume, the ejection fraction is arrived at.

Referring again to FIG. 2, the modulated carrier signal developed between the intra-cardiac electrodes are applied to a sense amplifier 30. The signal is then directed to microprocessor 34 which typically includes a bus structure 36 whereby address representing signals, data signals and control signals may be transmitted there over to effect storage and readout of data and programs from a ROM memory 38 and a RAM memory 40 connected to that bus.

In the embodiment of FIG. 2, the tip electrode 16 on the lead 12 is also connected to a QRS detector circuit 42 whose output on line 44 is applied to the microprocessor 34. The purpose of this input will be described in greater detail below.

The output from the microprocessor 34 is used to control the variable rate pulse generator 46 whose output is then applied via lead 12 and stimulating electrode 16 to the heart to evoke a paced response in the absence of normal cardiac activity. If the variable rate pulse generator 46 is an analog arrangement, the computed EF value will be converted to an analog signal. If the pulse generator 46 is a digital device, the data word representative of EF will be added to a rate register to alter the base rate of the pulse generator, all as is known in the art.

Referring again to FIGS. 1 and 2, the QRS detect circuit 42 produces a trigger signal to the microprocessor 34 upon the occurrence of a natural R-wave or at the occurrence of a paced beat. The trigger input to the microprocessor causes the digitized value of the end-diastolic volume of the right ventricle to be sampled and stored in the RAM 40 and it also initiates a timing interval on an internal timer (not shown) in the microprocessor which may be in the range of from 150 to 300 milliseconds. At the expiration of this time interval, the digitized value of the right ventricular volume will again be stored in the RAM 40. The time interval programmed into the microprocessor's timer is such that the contraction of the heart is nearly completed and the right ventricular volume is at its minimum. With these two data inputs stored, the microprocessor next executes a program to compute from the data the ejection fraction and a quantity directly related thereto is used to modify the escape interval of the variable rate pulse generator 46 in accordance with a predetermined conversion algorithm.

It can be seen, then, that a cardiac pacemaker configured as in FIG. 2 will have a rate-adaptive property where the pacing rate is made to increase from a base or at-rest rate to a higher rate based upon an increase in the ejection fraction of the ventricle.

Figure 3:
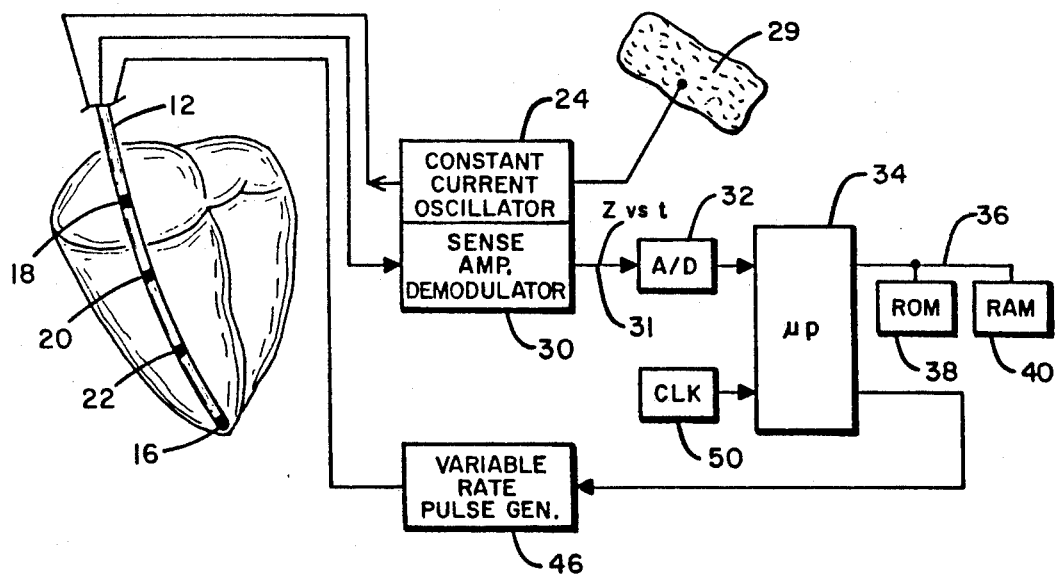
FIG. 3 is a schematic block diagram of an alternative embodiment of the present invention.
Figure 4:
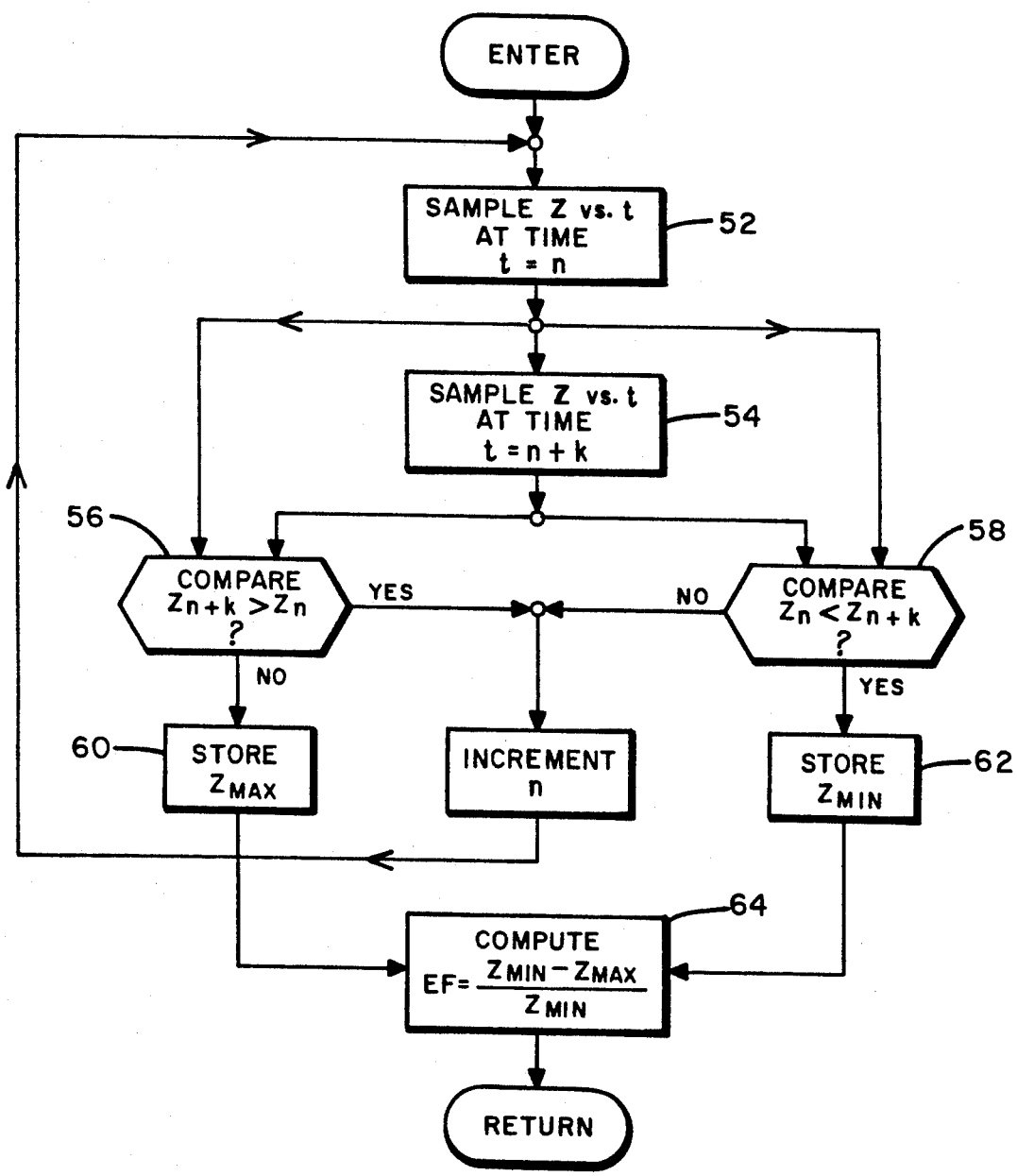
FIG. 4 is a software flow diagram of the subroutine used in the microprocessor of FIG. 3 for computing ejection fraction.

In the embodiment of FIG. 2, end-diastolic volume is measured at the occurrence of a R-wave or at the time of a paced beat while end-systolic volume is measured a predetermined time following the occurrence of the R-wave or paced beat. In the embodiment of FIG. 3, end-diastolic and end-systolic volumes are determined by detecting the maximum and minimum of the right ventricular volume waveform 28 of FIG. 1. A constant current oscillator 24 applies a high frequency carrier signal between the pacemaker can, a portion of which is shown at 29, and electrodes 16 on the lead 12, while a sense amplifier/demodulator circuit 30 senses the amplitude modulated carrier signal developed between sense electrodes 18 and 20 and demodulates the carrier to produce an impedance vs. time (Z vs. t) analog signal on line 31. This signal is digitized in the analog-to-digital converter 32 and the resulting digital quantity is applied to a data input of the microprocessor 34. Again, microprocessor 34 has a bus 36 to which a program-storing ROM 38 and a data-storing RAM 40 are connected. The microprocessor 34 is programmed to execute the routine illustrated by the flow diagram of FIG. 4 to compute ejection fraction and the computed result is applied to the variable rate pulse generator 46 to alter its escape interval from a lower, at-rest rate to a higher rate which is based upon physiologic demand.

To compute the ejection fraction, at predetermined incremental time intervals determined by the clock 50, the data input from the A/D converter 32 is sampled and stored in the RAM 40 as indicated by block 52. At a predetermined later time, the digitized version of the Z vs. t waveform is also sampled and stored in the RAM 40 as indicated by block 54.

Once two samples are stored, two tests represented by blocks 56 and 58 are carried out to determine whether the impedance at time n+k is greater than the impedance at time n and whether the impedance at time n is less than the impedance at time n+k. If the test performed at block 56 reveals that the impedance at time n+k is greater than that at time n, the value of n is incremented by a predetermined time value and a new set of samples is taken, as represented by blocks 52 and 54. This process continues until the comparison 56 shows that the indicated test is not true. At that point, the maximum value of the impedance ($Z_{max}$) has been determined and is stored as indicated by block 60.

In a similar fashion, if the test indicated in block 58 is not true, n is incremented and two new samples represented by blocks 52 and 54 are taken. When the test criteria reflected in block 58 is true, it is known that the minimum impedance point ($Z_{min}$) has been determined and that minimum value is stored in the ROM 40 as reflected by block 62 in FIG. 4.

Once the values of $Z_{max}$ and $Z_{min}$ are determined, it is possible to compute ejection fraction by subtracting $Z_{max}$ from $Z_{min}$ and dividing the result by $Z_{min}$ (block 64).

In the same fashion, the ratio of $Z_{max}$ to $Z_{min}$ corresponds to the residual fraction and because residual fraction is contractility dependent, it may be employed as a rate controlling parameter for a rate adaptive cardiac pacemaker.

It is contemplated that ejection fraction may be computed several times over successive heart beats and that a running average for several iterations be used to modify the pacing rate of the variable rate pulse generator 46 to determine its escape interval.

It is also contemplated that since the relationship between changes in end-diastolic impedance and resulting changes in end-systolic impedance may be non-linear under rest conditions, a correction factor may need to be stored in RAM 40 to make the resulting ejection fraction even more independent of preload modifications not associated with increased metabolic demands.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A rate adaptive cardiac pacemaker comprising, in combination:
   (a) a pulse generator having timing means for establishing the rate at which cardiac stimulating pulses are produced;
   (b) means for applying said stimulating pulses to cardiac tissue;
   (c) means for developing a control signal proportional to at least one of residual fraction and ejection fraction of the heart; and
   (d) means for applying said control signal to said timing means for varying the rate at which said cardiac stimulating pulses are produced as a function of the heart's contractility.

2. The rate adaptive cardiac pacemaker as in claim 1 wherein said means for developing a control signal proportional to the ejection fraction of the heart comprises:
   (a) means for developing a first signal proportional to the stroke volume of the heart;
   (b) means for developing a second signal proportional to the end-diastolic volume of the heart; and
   (c) means for producing said control signal as the ratio of said first signal to said second signal;
   (d) means for compensation of non linearity between changes of end-diastolic volumes and end-systolic volumes when metabolic demand is stable.

3. The rate adaptive cardiac pacemaker as in claim 2 wherein said means for developing said first and second signals includes intracardiac impedance sensing means.

4. The rate adaptive cardiac pacemaker as in claim 3 wherein said intracardiac impedance sensing means includes:
   (a) means for applying an alternating current carrier voltage of a predetermined frequency between two spaced points in the heart; and
   (b) means for sensing instantaneous changes in amplitude of said alternating current carrier voltage due to systolic activity of the heart.

5. The rate adaptive cardiac pacemaker as in claim 4 wherein said means for developing said first signal includes:
   (a) means for computing the difference between the maximum and minimum amplitude excursions of said alternating current carrier voltage.

6. The rate adaptive cardiac pacemaker as in claim 4 wherein said means for developing said second signal includes:
   (a) means for measuring the minimum amplitude excursions of said alternating current carrier voltage.

7. The rate adaptive cardiac pacemaker as in claim 1 wherein said means for developing a control signal proportional to residual fraction includes:
   (a) means for developing a first signal proportional to end-systolic volume of the heart;
   (b) means for developing a second signal proportional to the end-diastolic volume of the heart; and
   (c) means for dividing said first signal by said second signal.

8. A rate adaptive pacemaker comprising, in combination:
   (a) an electronic pulse generator having variable timing means for determining the rate at which cardiac stimulating pulses are produced;
   (b) means for applying said pulses to the heart;
   (c) means for sensing intracardiac impedance variations occasioned by systolic events;
   (d) means responsive to said means for sensing intracardiac impedance for computing the ejection fraction of the heart; and
   (e) means for adjusting said timing means in relation to the computed ejection fraction.

9. The rate adaptive pacemaker as in claim 8 wherein said means for computing ejection fraction comprises:
   (a) means for sampling the amplitude of the intracardiac impedance upon the occurrence of an R-wave or a cardiac stimulating pulse in the absence of an R-wave to establish end-diastolic volume (EDV);
   (b) means for at least temporarily storing a EDV value proportional to the sampled amplitude;
   (c) means for sampling the amplitude of the intracardiac impedance at a predetermined time following the occurrence of the R-wave or cardiac stimulating pulse to establish an end-systolic volume value (ESV);
   (d) means for subtracting the ESV value from the stored value to determine stroke volume value (SV); and
   (e) means for dividing the SV value by the EDV value.

10. The rate adaptive pacemaker as in claim 8 wherein said means for computing ejection fraction comprises:
    (a) means for sampling the minimum excursion of said intracardiac impedance variation to establish end-diastolic value (EDV);
    (b) means for temporarily storing the EDV value;
    (c) means for sampling the maximum excursion of said intracardiac impedance variation to establish an end-systolic volume value (ESV);
    (d) means for temporarily storing the ESV value; and
    (e) means for computing the ratio (ESV - EDV)/EDV.

* * * * *